(12) United States Patent
Pisharodi

(10) Patent No.: US 6,264,655 B1
(45) Date of Patent: *Jul. 24, 2001

(54) CERVICAL DISK AND SPINAL STABILIZER

(76) Inventor: Madhavan Pisharodi, 942 Wild Rose La., Brownsville, TX (US) 98530

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/904,856

(22) Filed: Aug. 1, 1997

Related U.S. Application Data

(63) Continuation-in-part of application No. 08/475,211, filed on Jun. 7, 1995.

(51) Int. Cl.$^7$ .................................................. A61B 17/56
(52) U.S. Cl. ............................................... 606/61; 606/71
(58) Field of Search ............................... 606/61, 60, 72, 606/73; 623/17

(56) References Cited

U.S. PATENT DOCUMENTS

| 3,334,624 | 8/1967 | Schneider et al. . |
| 3,486,505 | 12/1969 | Morrison . |
| 4,349,921 | 9/1982 | Kuntz . |
| 4,599,086 | * 7/1986 | Doty ........................................ 623/17 |
| 4,657,550 | 4/1987 | Daher . |
| 4,711,232 | 12/1987 | Fischer et al. . |
| 4,759,769 | 7/1988 | Hedman et al. . |
| 4,834,757 | 5/1989 | Brantigan . |
| 4,863,476 | 9/1989 | Shepperd . |
| 4,932,975 | 6/1990 | Main et al. . |
| 5,015,247 | 5/1991 | Michelson . |
| 5,059,193 | 10/1991 | Kuslich . |
| 5,171,278 | 12/1992 | Pisharodi . |
| 5,171,279 | * 12/1992 | Matthews ................................. 623/17 |
| 5,306,309 | 4/1994 | Wagner et al. . |

(List continued on next page.)

FOREIGN PATENT DOCUMENTS

| 2151481 | 3/1995 | (CA) . |
| 3729600 | 3/1989 | (DE) . |
| 0042271 | 12/1981 | (EP) . |
| 0260044 | 3/1988 | (EP) . |
| 0307241 | 3/1989 | (EP) . |
| 0662082 | 2/1982 | (SU) . |
| 9214423 | 3/1992 | (WO) . |
| 9508306 | 3/1995 | (WO) . |
| 9526164 | 10/1995 | (WO) . |

Primary Examiner—Michael Buiz
Assistant Examiner—Jonathan D. Goldberg
(74) Attorney, Agent, or Firm—Mark R. Wisner

(57) ABSTRACT

A middle expanded, removable disk implant for stabilizing adjacent cervical vertebrae. The implant is substantially rectangular in cross-sectional shape with a minimal height and a width greater than the height. The implant is detachably mounted to an applicator for insertion into the anatomical region between two adjacent cervical vertebrae from which the intervertebral disk has been removed, and once inserted, is positioned by anterior-posterior movement in the disk space to the position in which both the expanded, larger width middle portion and the smaller diameter end portions of the implant engage the bodies of the adjacent vertebrae and the implant is then rotated to bring the sides of the rectangularly-shaped implant defining the width of the implant, with its larger dimension, into engagement with the bodies of the adjacent vertebrae. A lock, in the form of a stabilizer bar, is then secured to the implant to prevent further rotation thereof. The stabilizer bar includes structure which prevents relative rotation between the stabilizer bar and the implant and structure which protrudes into the space between the cervical vertebrae to prevent rotation relative to the vertebrae.

20 Claims, 9 Drawing Sheets

U.S. PATENT DOCUMENTS

| | | |
|---|---|---|
| 5,324,292 | 6/1994 | Meyers . |
| 5,458,641 * | 10/1995 | Ramirez Jimenez .................. 623/17 |
| 5,591,235 * | 1/1997 | Kuslich ................................ 623/17 |
| 5,653,762 | 8/1997 | Pisharodi . |
| 5,658,336 | 8/1997 | Pisharodi . |
| 5,683,391 * | 11/1997 | Boyd ..................................... 606/61 |
| 5,755,796 * | 5/1998 | Ibo et al. ............................... 623/17 |

* cited by examiner

CERVICAL DISK AND SPINAL STABILIZER

CROSS REFERENCE TO RELATED APPLICATION

The present application is a continuation-in-part of co-pending prior application Ser. No. 08/475,211, filed Jun. 7, 1995.

BACKGROUND OF THE INVENTION

The present invention relates to an intervertebral disk stabilizing implant and a method of stabilizing two adjacent vertebrae. More specifically, the present invention relates to rectangularly-shaped disk implants which are expanded in the middle portion and are used for spinal fusion.

Treatment of a herniated disk in the neck and in the lumbar region continues to be a challenging field of medicine. The classical treatment for a ruptured disk is diskectomy, i.e., removal of the disk from between the vertebrae. In this process, all or a portion of the intervertebral disk is removed, leaving a defect which may continue to bother the patients throughout the rest of their lives. An additional procedure is to replace the disk space with a bone graft, usually bone chips cut from the patient's iliac crest, bringing about fusion of the vertebrae above and below the disk, eliminating the empty space between the vertebrae.

No prosthetic disk has been shown to be safe and efficacious to date, so the best alternative treatment currently available is a simple and safe way to fuse the adjacent vertebrae. However, diskectomy with fusion is not ideal because the replaced bone does not have the function of the cartilaginous tissue of the disk, i.e. no cushioning effect, and has complications because of several factors. First, conventional bone plugs used to pack the disk space do not conform to the space of the disk because the disk bulges maximally in the center. The disk space is wider in the middle and narrower at its anterior and posterior ends. For this reason, the various bone plugs which are currently available commercially have only four contact points, i.e. at the front and back of the disk space. Secondly, access to the disk is from the side of the dorsal spine of the adjacent vertebrae, leaving a space that is "off-center" relative to the bodies of the adjacent vertebrae such that the stability of the implant is even more problematical than might be apparent from the limited contact resulting from the shape of the intervertebral space. Another complication is the possibility of infection or other conditions which may require the removal of the implant. Also, if the bone pieces do not fuse, they may eventually extrude out of the disk space, causing pressure on the nerve roots.

Various prosthetic disk plugs, or implants, are disclosed in the art, but all are characterized by limitations of not conforming to the shape of the disk space, lack of stability when inserted off-center, inability to be removed, or other disadvantages. For instance, U.S. Pat. No. 4,863,476 (and its European counterpart, EP-A-0260044) describes an elongated body divided longitudinally into two portions having a cam device movable therebetween for increasing the space between the two body portions once inserted into the disk space. However, that device is generally cylindrical in shape such that the only contact points between the device and the vertebral bodies are at the front and back of the disk space, creating increased likelihood of instability and generally rendering that device unsuitable for use after partial diskectomy. The art also discloses intervertebral disk prostheses (e.g., U.S. Pat. Nos. 3,867,728, 4,309,777, 4,863,477 and 4,932,969 and French Patent Application No. 8816184) which may have more general contact with the adjacent disks, but which are not intended for use in fusion of the disks. The art also includes spinal joint prostheses such as is described in U.S. Pat. No. 4,759,769, which is again not indicated for use when fusion is the preferred surgical intervention.

The problem of maintaining the spacing between vertebrae is particularly acute in the cervical vertebrae. The surgery itself is not as difficult as in the lumbar spine because access to the intervertebral space is from the front in the cervical spine, e.g., ventrally to the patient. Bone chips are not substantial enough to maintain the spacing between vertebrae, so the accepted surgical method to maintain spacing between adjacent vertebrae in the cervical spine is to scoop out the entire damaged disk, drill a hole into the intervertebral space, and insert a plug of the patient's bone into the space between vertebrae.

However, the cervical vertebrae are smaller than the vertebrae in the other portions of the spinal column such that there is little tolerance for anterior or posterior movement of the implant in the disk space such as may occur before the fusion is complete. Specifically, because of the relatively small tolerances, almost any movement posteriorally in the disk space imperils the nerves of the spinal cord. Bone plugs have no structure to resist such movement. Consequently, the hole into which the bone plug is inserted is slightly undersized relative to the plug so that the ligaments on either side of the spinal column help hold the plug in place by compressing the plug between vertebrae. Even so, the implant can move in the intervertebral space, so there is a need for a spinal implant for stabilizing adjacent vertebrae which maintains sufficient space between the vertebrae to allow the spinal nerves to pass between the processes of the cervical vertebrae without impingement by the vertebrae and which does not allow anterior or posterior movement of the implant in the disk space.

Similarly, the bone chips packed into the intervertebral space around the plug can be extruded out of the space posteriorally into contact with the spinal cord or the spinal nerves by the compression provided by the ligaments which help hold a bone plug in place. There is, therefore, a need for an implant, and a method of stabilizing adjacent vertebrae, which eliminates the possibility of impingement of the nerves of the spinal cord and/or the spinal nerves. In that same manner, there is a need for an implant and method for stabilizing more than two adjacent vertebrae of the spinal column without imperiling the spinal cord and spinal nerves and without placing screws into the spinal bodies.

SUMMARY OF THE INVENTION

These objects are provided by a cervical disk stabilizer constructed in accordance with the teachings of the present invention which comprises an elongate member having a substantially rectangular cross-sectional shape for inserting between adjacent cervical vertebrae and a stabilizer bar for detachably mounting to one end of the elongate member to prevent relative rotation therebetween. An ear is formed on the stabilizer bar for inserting between the adjacent cervical vertebrae, and because the stabilizer bar is mounted to the elongate member in such a way as to prevent relative rotation, if the elongate member even starts to rotate in the space between adjacent cervical vertebrae, the ear contacts one of the bodies of the adjacent vertebrae to prevent rotation of the elongate member. In a preferred embodiment, the stabilizer bar is elongate and the long axis of the stabilizer bar is mounted orthogonally to the longitudinal axis of the elongate member.

BRIEF DESCRIPTION OF THE DRAWINGS

Referring now to the figures, a perspective view of a preferred embodiment of a cervical stabilizer constructed in accordance with the teachings of the present invention is shown in FIG. 1.

DETAILED DESCRIPTION OF THE INVENTION

Figure 1:
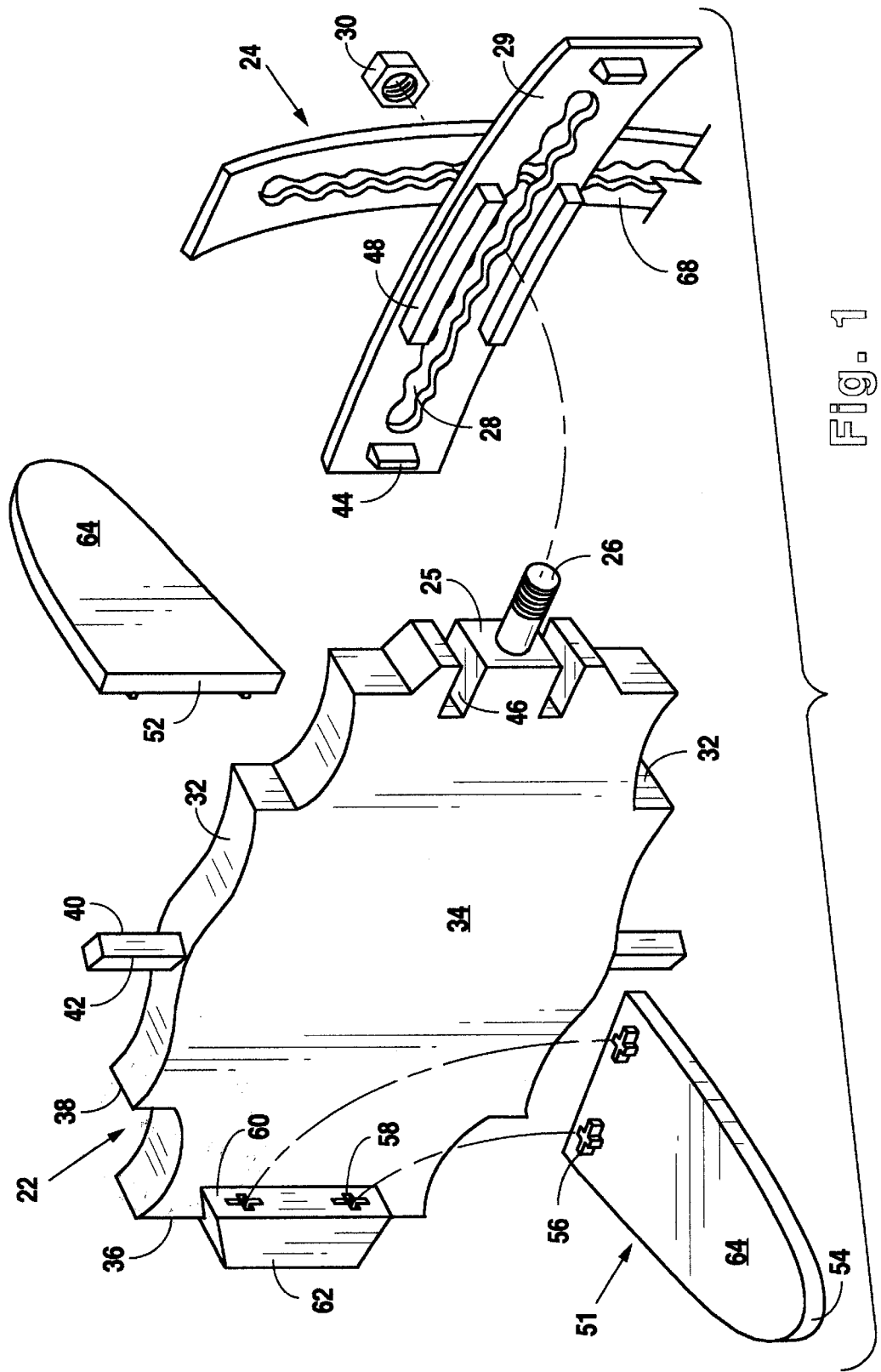

Referring now to the figures, a preferred embodiment of a cervical stabilizer constructed in accordance with the teachings of the present invention is shown in FIG. 1. The stabilizer is comprised of an elongate implant 22, a lock which is indicated generally at reference numeral 24, and means for detachably mounting the lock to one end 25 of the implant 22. In the presently preferred embodiment shown, the mounting means takes the form of a bolt, or threaded post, 26 passing through a bore 28 in the stabilizer bar 29 comprising lock 24, the threads of post 26 engaging complementary threads in the nut 30 received on the end of post 26.

Figure 2:
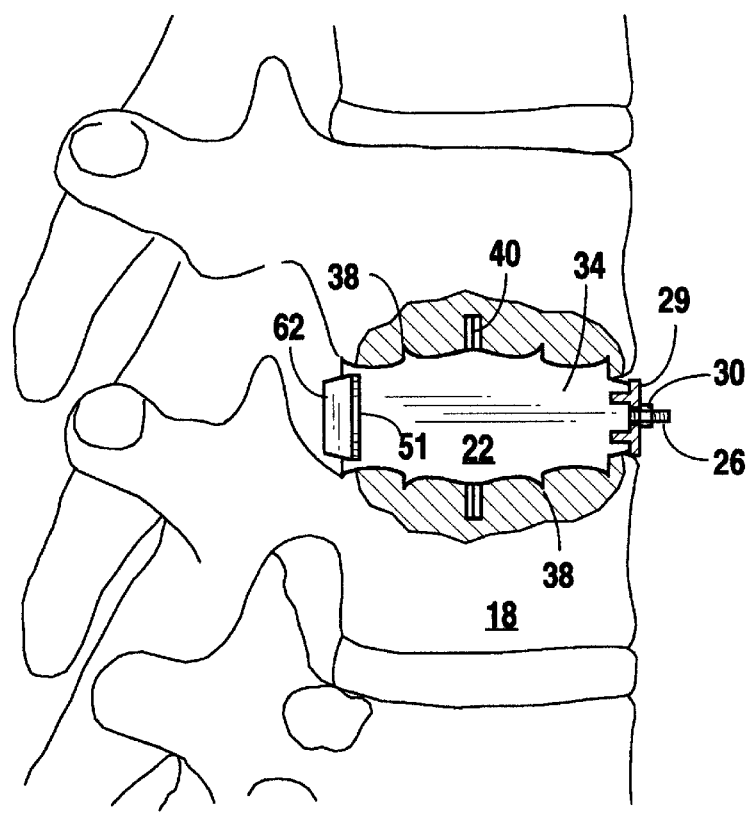
FIG. 2 is a side view of the human spinal column showing the cervical stabilizer of FIG. 1 inserted in the intervertebral space and having a portion of the adjacent vertebrae cut away to show the manner in which the stabilizer interacts with the adjacent vertebrae.

In more detail, implant 22 is an elongate member comprised of first and second sides 32 and third and fourth sides 34 providing a substantially rectangular-shaped cross-sectional shape. The height H of the rectangularly shaped cross-section is defined by first and second sides 32 and the width W is defined by third and fourth sides 34 and, as is apparent by comparison of H and W, the height H of implant 22 is less than the width W. As will be explained below, H is minimized to facilitate insertion of the second end 36 into, and positioning of implant 22 in, the disk space from which all or a portion of the intervertebral disk 20 was removed and W is maximized to provide the desired stabilization to adjacent vertebrae 16 and 18 (see FIG. 2). Third and fourth sides 34 are arched from one end of implant 22 to the other to provide the portion of implant 22 intermediate the ends 25 and 36 with a width W' which is larger than the width W" at the ends 25 and 36. Because the sides 32 of implant 22 are substantially flat and the sides 34 are arched from one end 25 to the other end 36, implant 22 is described as being a biplanar, bi-convex implant.

The bi-convex sides 32 of implant 22 are provided with a plurality of teeth 38 for biting into the adjacent vertebrae 16 and 18 as will be explained in more detail below. The end 36 of implant 22 is formed in a blunt, preferably flat, shape to reduce the likelihood of injury to the nerves of the spinal chord during insertion into the disk space.

In the preferred embodiment shown, implant 22 is provided with cleats 40 formed integrally therewith; the cleats 40 may be threaded onto or otherwise assembled to the implant 22 in a manner which will be apparent to those skilled in the art from this description of that structure. The cleats 40 are formed in the shape of a diamond and oriented so that the portion of the cleat 40 which first contacts the body of the adjacent spinal vertebrae when rotated in the disk space as described below is a sharp, leading edge 42 to facilitate biting into the bone of the vertebrae 16 and 18. Those skilled in the art who have the benefit of this disclosure will recognize that the cleat 40 may be formed in other shapes or configurations, e.g., hooked, pointed, barbed, toothed, or other shape which accomplishes the intended function of biting into the bone of the adjacent vertebrae so as to decrease the likelihood of movement of the implant 22 in an anterior or posterior direction (relative to the disk space) once inserted into the intervertebral space as described below. Similarly, the teeth 38 need not be shaped in the shape shown in FIG. 1 to decrease the likelihood of anterior-posterior movement of the implant 22 in the disk space. The teeth 38 can be made pointed, beveled to a point in opposite directions, or in any other configuration which will increase the resistance to movement of implant 22 relative to the bone comprising the adjacent vertebrae 16 and 18.

In the preferred embodiment shown, lock 24 is comprised of a stabilizer bar 29 which is detachably mounted to the end 25 of implant 22 and serves to prevent rotation of implant 22 relative to the adjacent vertebrae 16 and 18 when the implant 22 is inserted between the vertebrae. In the embodiment shown in FIG. 1, the stabilizer bar 29 is mounted to implant 22 on post 26 which is formed integrally with the end 25 of implant 22. As will be apparent from the following description, the end 25 of implant 22 is the end which is positioned anteriorally when implant 22 is inserted between the two cervical vertebrae 16 and 18. The post 26 is threaded to receive a nut 30 for retaining the stabilizer bar 29 thereon. Means is provided for preventing rotation of stabilizer bar 29 relative to implant 22 when stabilizer bar 29 is mounted thereto in the form of the slots 46 formed on the end 25 of implant 22 for receiving a complementary-shaped key 48 formed on stabilizer bar 29; those skilled in the art who have the benefit of this disclosure will recognize that the slot 46 may be located on the implant 22 and the key 48 may be located on the stabilizer bar 29 without any difference in the manner in which those component parts function.

Figure 3:
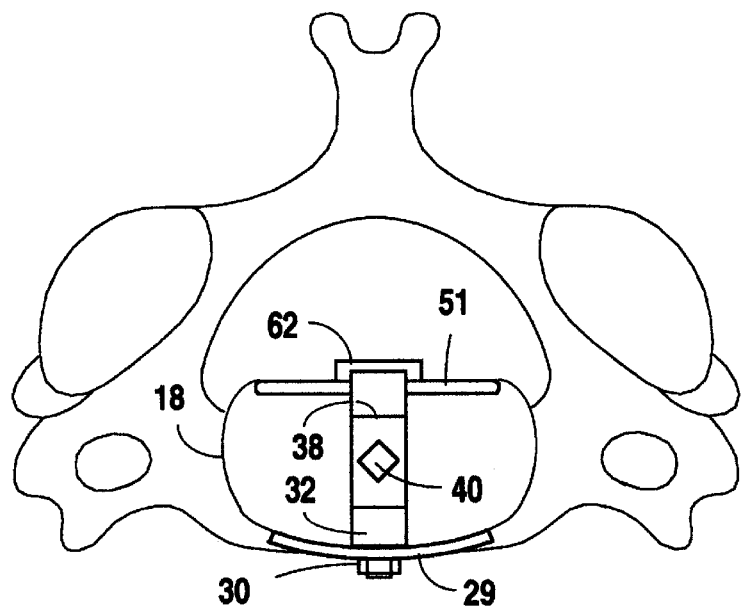
FIG. 3 is a top plan view of a single cervical vertebra showing the anterior-posterior positioning of the cervical stabilizer of FIG. 1 relative to the body of the vertebra.

As best shown in FIG. 3, stabilizer bar 29 is elongate and is mounted to the end 25 of implant 22 so that the longitudinal axis of the stabilizer bar is positioned at an angle of about 90° relative to the longitudinal axis of implant 22. The ventral surfaces of the bodies of the adjacent vertebrae 16 and 18 are rounded when viewed along the axis of the spinal column and shown in FIG. 3, and to accommodate that rounded shape, the stabilizer bar 29 is also curved to approximate that shape. Stabilizer bar 29 is provided with an ear 44, preferably at or near both ends thereof, for inserting between the adjacent vertebrae 16 and 18 when the implant 22 to which stabilizer bar 29 is mounted is positioned between the adjacent cervical vertebrae. The ears 44 protrude into the disk space between the bodies of the adjacent vertebrae 16 and 18, and are provided with a vertebrae bearing surface 50 on the top and bottom surfaces thereof which, when stabilizer bar 29 is mounted to implant 22, which is in turn held in place against anterior-posterior movement by the cleats 40 and teeth 38, prevent relative rotation between vertebrae 16 and 18 and implant 22. In this manner, the stabilizer bar 29 locks implant 22 in place between the vertebrae 16 and 18.

As noted above, the space around the implant 22 in the intervertebral space is preferably packed with bone chips (not shown) to facilitate fusion of the adjacent vertebrae, the implant 22 maintaining the proper spacing between the vertebrae. As also noted above, it is important to prevent extrusion of the bone chips posteriorally into engagement with the spinal cord and/or the spinal nerves. In order to prevent such extrusion, the cervical stabilizer of the present invention is provided with elongate spinal cord protectors 51, the long axis of which extends at approximately a 90° angle, e.g., orthogonally to the long axis of the implant 22 as shown in FIG. 3. The protectors 51 extend orthogonally from the first and second sides 32 of implant 22, e.g., laterally when the implant is implanted into the patient, within the disk space to close off the posterior aspect of the disk space. In this manner, the protectors 51 prevent, or at least reduce the likelihood of, extrusion of the bone chips packed into the disk space posteriorally into engagement with the spinal cord.

As will be discussed in more detail below, the surfaces of the bodies of the vertebrae 16 and 18 adjacent the disk space are slightly concave such that the disk space is shaped somewhat like the space between two inverted saucers. Due to the shape of the disk space, the posterior opening of the disk space narrows near the edges of the vertebral bodies, hence the distal ends 54 of protectors 51 are of smaller vertical dimension (vertical with reference to the patient's spinal column when the implant is implanted and the protectors 51 are positioned on the implanted implant in the manner described below) than the proximal ends 52 adjacent implant 22.

Again due to the shape of the disk space, it is inconvenient to insert the implant 22 into the disk space with the protectors 51 in the position shown in FIG. 3, e.g., with the longitudinal axis of the protectors 51 at approximately a right angle to the long axis of implant 22. Means is therefore provided for positioning the protectors in that orthogonal position after the implant 22 has been inserted into the disk space. In the embodiment shown in FIG. 1, the positioning means takes the form of snap fit posts 56 formed on each of the protectors 51 for press-fitting into complementary slots 58 formed in the surface 60 of an end stop 62 which is integral with the end 36 of implant 22. The surface 60 is oriented at approximately a 90° angle to the first and second surfaces 32 of implant 22 and the posts 56 are formed on one of the sides 64 of protectors 51 so that when the posts 56 are press fit into the slots 58, the long axes of the protectors 51 are positioned at the same orthogonal angle (relative to the longitudinal axis of implant 22) as the surface 60.

Figure 4:
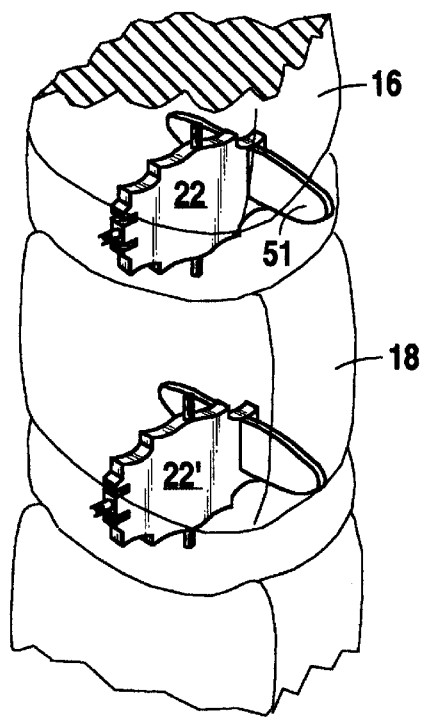
FIG. 4 is a partially schematic, perspective view of the ventral aspect of the vertebral bodies of three adjacent cervical vertebrae having the cervical stabilizer of FIG. 1 inserted between each adjacent vertebrae.
Figure 5:
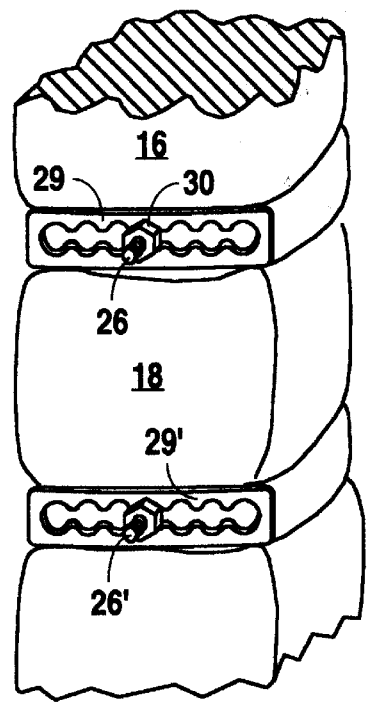
FIG. 5 is a partially schematic view of three adjacent cervical vertebrae similar to the view shown in FIG. 4 showing the two cervical stabilizers before connection with a spinal stabilizer constructed in accordance with the teachings of the present invention.
Figure 6:
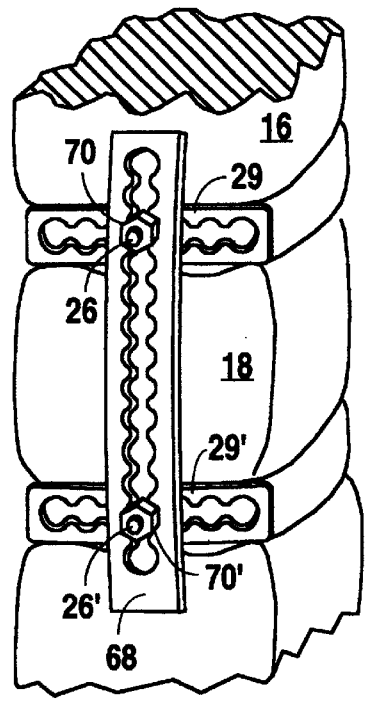
FIG. 6 is a partially schematic view of three adjacent cervical vertebrae similar to the view shown in FIG. 4 and having a spinal stabilizer connecting the two cervical stabilizers.

Referring now to FIGS. 4–6, a spinal stabilizer constructed in accordance with the teachings of the present invention which is comprised of the cervical stabilizer of the present invention is shown. Referring to FIG. 4, the bodies of three adjacent cervical vertebrae 16, 18, and 66 are shown in partially schematic, perspective view from the ventral side of the patient (the anterior, or front, of the disk space). A first cervical stabilizer 22 of the type described in the preceding paragraphs is shown in the space between the first and second vertebrae 16 and 18, respectively, and a second stabilizer 22', also of the type described in the preceding paragraphs, is shown in the space between the second and third vertebrae 18 and 66, respectively. As shown in FIG. 5, stabilizer bars 29 and 29' are mounted to each of the respective implants 22 and 22' on the respective posts 26 and 26' of each implant using nuts 30 and 30', respectively, in the manner described above. As shown in FIG. 6, connector 68 is then fastened to each of the posts 26 and 26' of implants 22 and 22' using a second set of nuts 70 and 70' to link the first and second implants 22 and 22', respectively, thereby providing support for fusion of three cervical vertebrae with all the advantages of the cervical stabilizer of the present invention.

Figure 7:
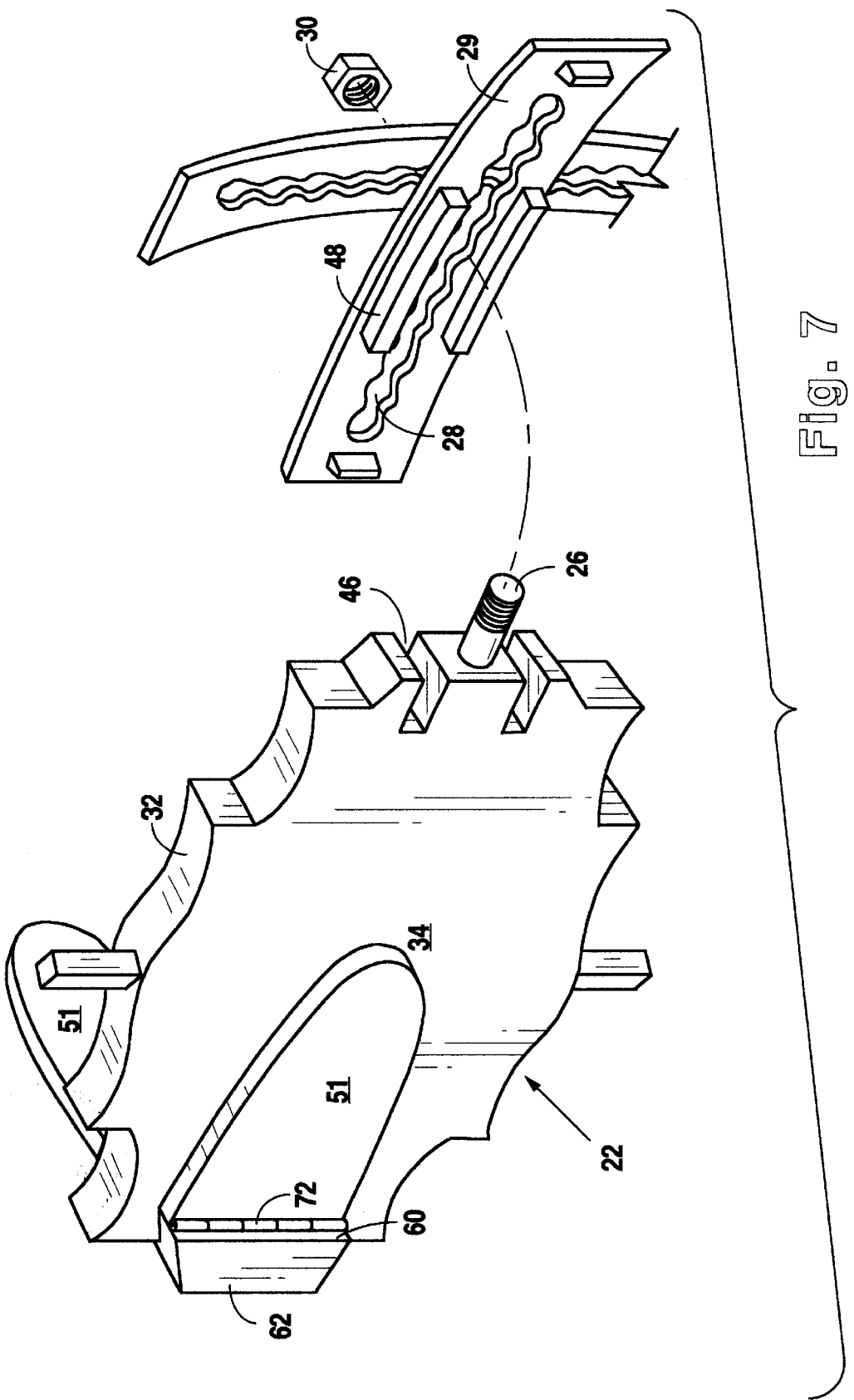
FIG. 7 is a perspective view of a second embodiment of a cervical stabilizer constructed in accordance with the teachings of the present invention.

Referring now to FIGS. 7–12, there are shown a number of alternative embodiments of the cervical stabilizer of the present invention. Referring first to FIG. 7, it can be seen why the connection between the protectors 51 and implant 22 is referred to herein as positioning means. In the embodiment shown in FIGS. 1–6, the positioning means for the protectors 51 took the form of press fit connectors formed by the posts 56 and slots 58 on the protectors 51 and end stop 62, respectively. In the embodiment shown in FIG. 7, the positioning means takes the form of a piano hinge 72 which connects the protector 51 to the end stop 62. The implant 22 shown in FIG. 7 is inserted into the intervertebral space with the protectors 51 in a first, folded position in which the longitudinal axes of the protectors 51 are substantially parallel to the longitudinal axis of the implant 22. After rotation of the implant 22 along the longitudinal axis thereof in the manner described above, the protectors 51 are pivoted from the first, folded position to the second, extended position in which the longitudinal axes of the protectors are substantially orthogonal to the longitudinal axis of the implant 22. To illustrate, the implant 22 shown in FIG. 7 is shown with one of the protectors 51 in the first, folded position and the other in the second, extended position.

In the embodiment shown in FIG. 7, the piano hinge 72 is formed on the end stop 62 near the point at which the end stop 62 and the third and fourth sides 34 of implant intersect. In this manner, the orthogonal surface 60 of end stop 62 acts to provide a stop to prevent the pivoting of the protector from the first to the second position and helps retain the protector 51 in the second, extended position.

Figure 8:
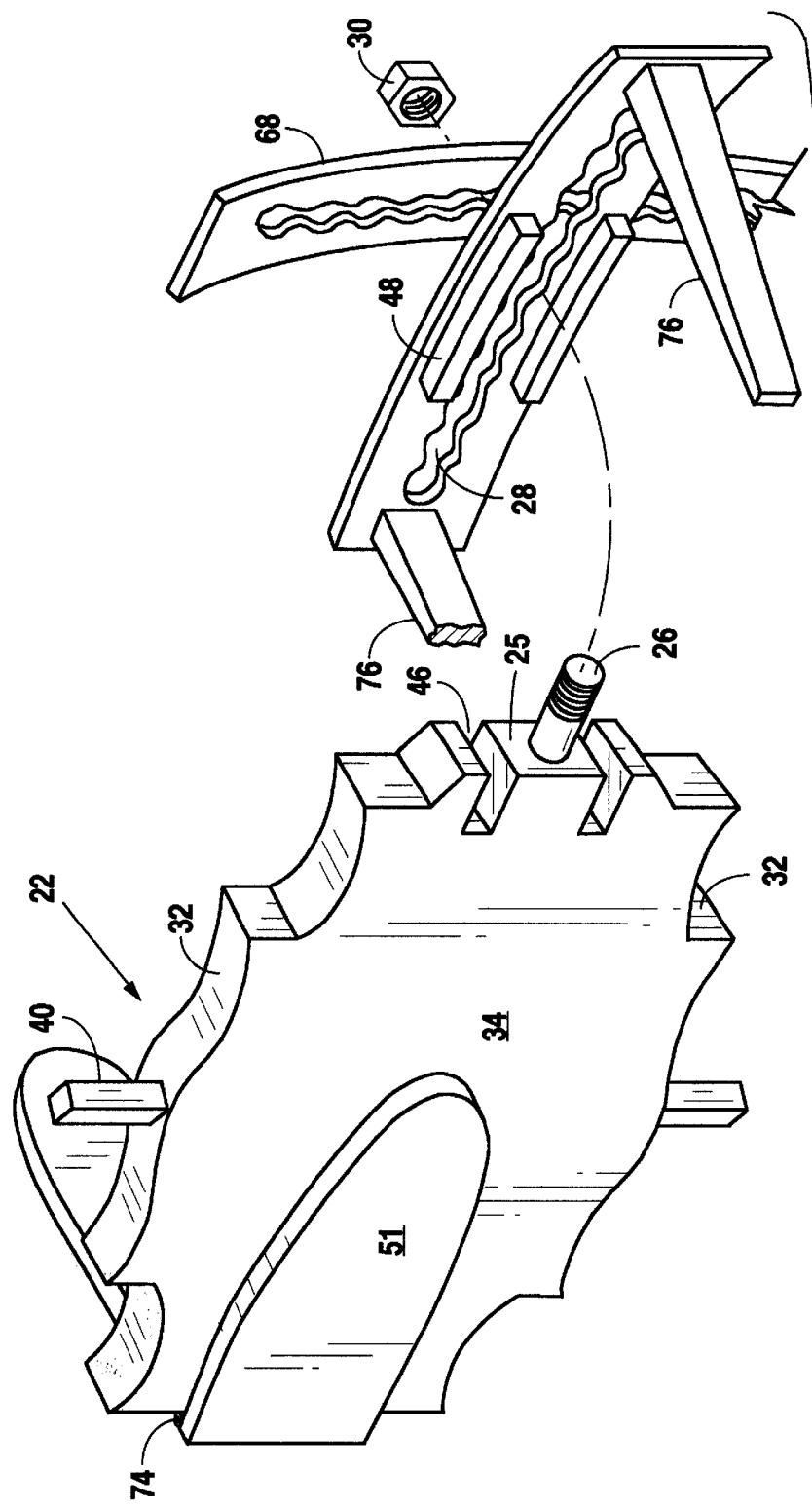
FIG. 8 is a perspective view of a third embodiment of a cervical stabilizer constructed in accordance with the teachings of the present invention.

Referring to FIG. 8, a second alternative embodiment is shown in which the protectors 51 are pivoted from a first, folded position to the second, extended position. In the embodiment shown in FIG. 8, the piano hinges 74 connecting protectors 51 to implant 22 are located on the end 36 of implant 22 so that, when the protectors 51 are pivoted to the extended position, their proximal ends 52 are pivoted into abutting relationship so as to resist further pivoting of the protectors 51 on piano hinges 74. A second variation of the cervical stabilizer of the present invention shown in FIG. 8 is a change in the shape of the ears on stabilizer bar 29 as compared to the shape of the ears 44 shown in the embodiments shown in FIGS. 1–7. Ears 76 extend from stabilizer bar 29 for a substantial distance so that, when the stabilizer bar 29 is mounted to implant 22, they project into the intervertebral space so that the vertebrae engaging surfaces 50 formed thereon engage the hard cortical bone of the adjacent vertebrae at the edges of the bodies of the adjacent vertebrae 16 and 18 (not shown in FIG. 8), thereby providing support for the adjacent vertebrae in a position located outwardly from the implant 22.

Figure 9:
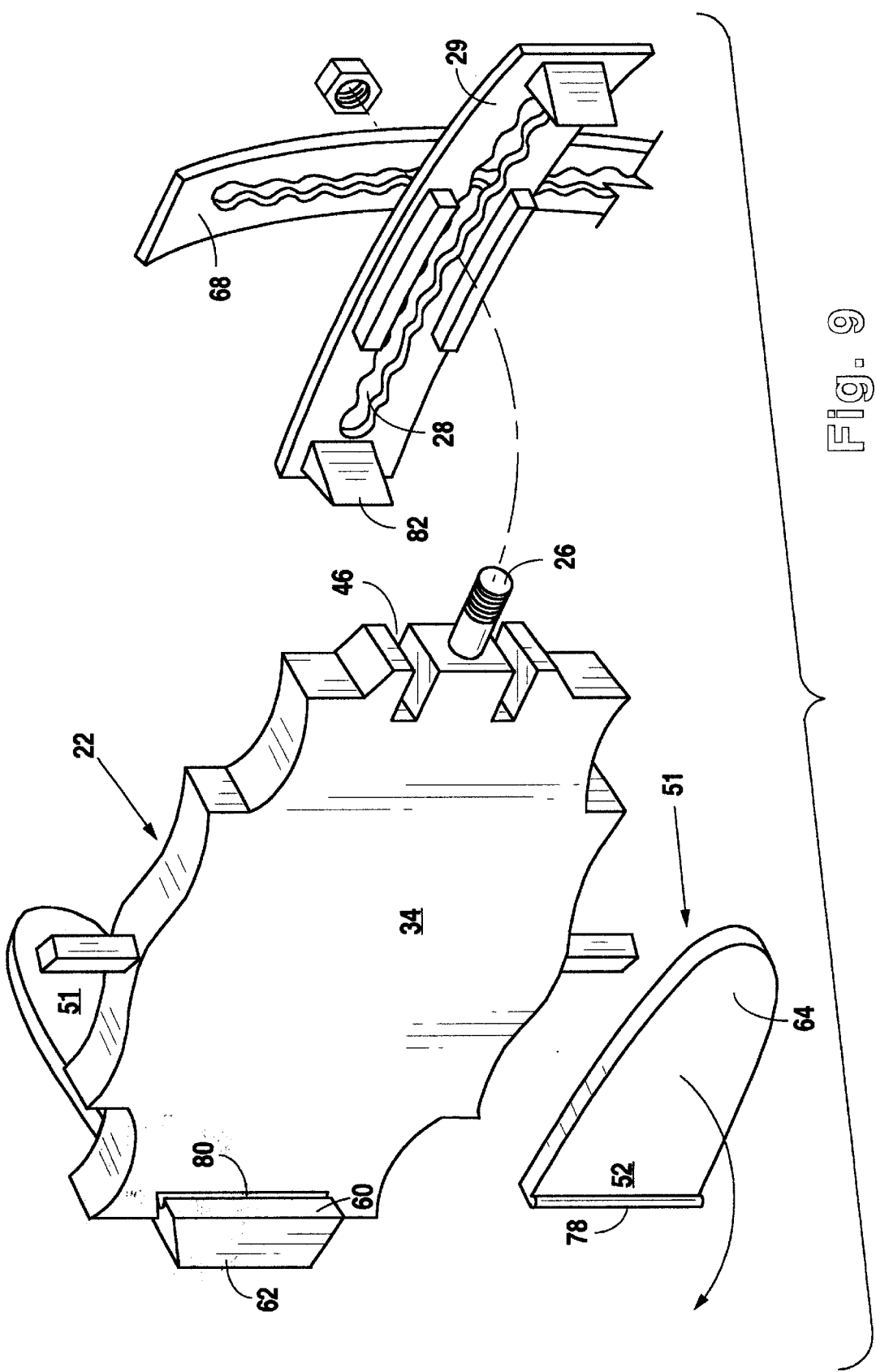
FIG. 9 is a perspective view of a fourth embodiment of a cervical stabilizer constructed in accordance with the teachings of the present invention.

Referring to FIG. 9, yet another embodiment of the cervical stabilizer of the present invention is shown. In the embodiment shown in FIG. 9, the protectors 51 are provided with a rolled edge 78 at the proximal end 52 thereof which is press fit into a complementary-shaped groove 80 formed in the orthogonal surface 60 of end stop 62. In this embodiment, the orthogonal surface 60 provides both a stop against which the protector is positioned when it is inserted into the disk space for press fitting into the groove 80 and the resistance to pivoting of the protector to an angle greater than about 90° from the longitudinal axis of implant 22 in the same manner as described above in connection with the embodiments shown in FIGS. 1–8. A second variation in the embodiment shown in FIG. 9 is seen in the shape and size of the ears 44. In the embodiment shown in FIG. 9, the ears 82 are shaped and sized so as to protrude into the disk space farther than the ears 44 of the embodiments shown in FIGS. 1–7 to provide additional vertebral surface against which the vertebral bearing surfaces 50 bear, but not so far as the ears 76 of the embodiment shown in FIG. 8.

Figure 10:
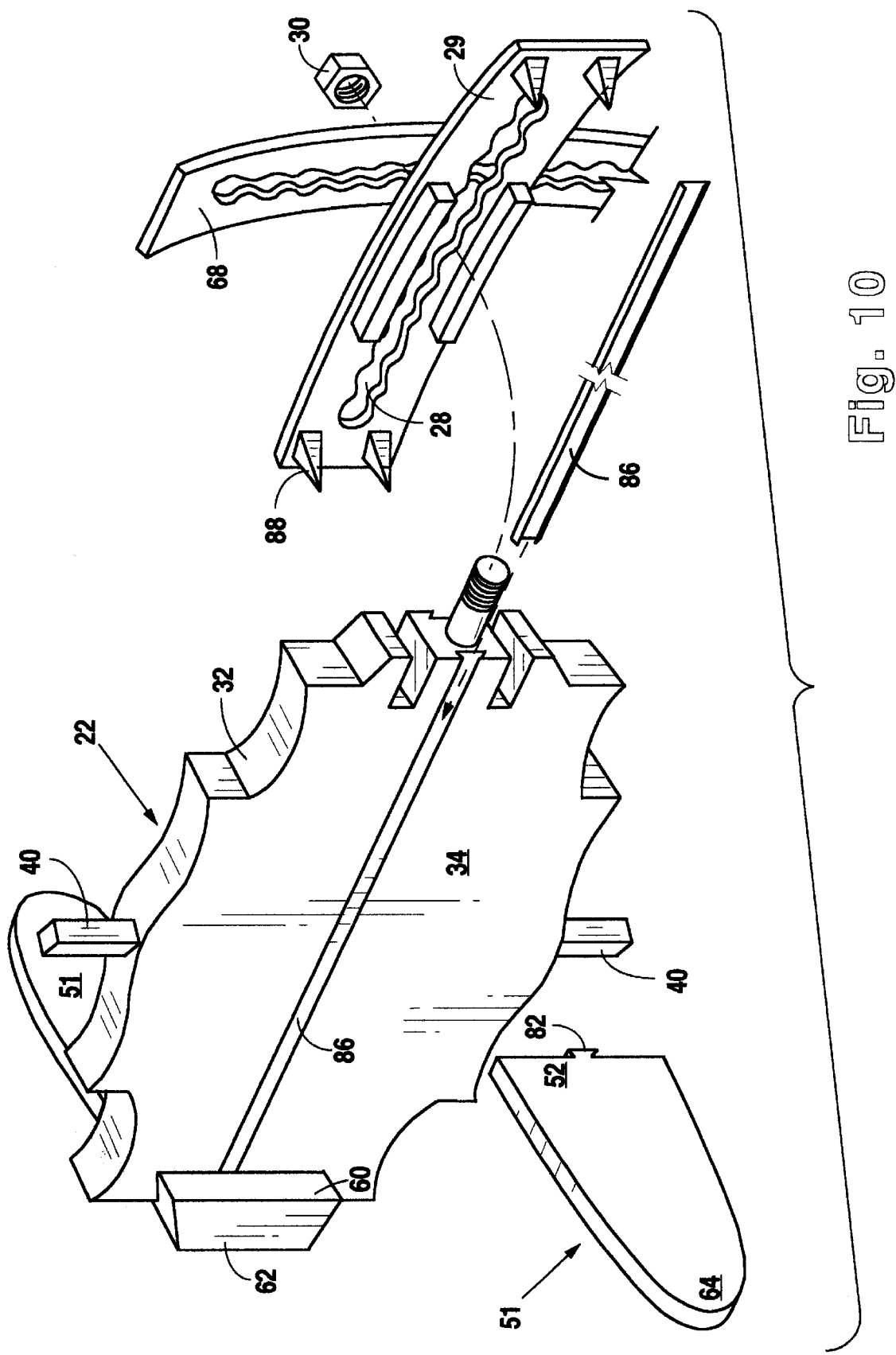
FIG. 10 is a perspective view of a fifth embodiment of a cervical stabilizer constructed in accordance with the teachings of the present invention.

Yet another alternative embodiment of the cervical stabilizer of the present invention is shown in FIG. 10. In the embodiment shown in FIG. 10, as in the embodiments shown in FIGS. 1–6 and 9, the protectors are assembled to the implant 22 after insertion of the implant 22 into the intervertebral space. In the embodiment shown in FIG. 10, the proximal ends 52 of protectors 51 are provided with a key 82 for sliding in the keyway 84 which runs the length of the third and fourth faces 34 of implant 22 along the longitudinal axis thereof until protectors 51 abut the orthogonal surface 60 of end stop 62, the latter providing the support described above. To prevent the protectors 51 from working back out of the keyway 84 toward the end 25 of implant 22, the implant shown in FIG. 10 is optionally provided with an elongate keeper 86 shaped to fit into and slide into the keyway 84 so that when the keeper 86 is inserted into the keyway 84 and the stabilizer bar 29 is mounted thereto, the keeper 86 prevents movement of the protectors 51.

Another embodiment of the ears on the stabilizer bar 29 is also shown in FIG. 10. In the embodiment shown in that figure, the vertebral bearing surfaces 50 on the stabilizer bar take the form of multiple, pointed barbs 88. If the spacing between adjacent vertebrae is not such that the ears 44 shown in the other figures fit between the bodies of the vertebrae, or if for some other reason a stabilizer bar having ears formed thereon cannot be utilized, it is still possible to prevent relative rotational movement between vertebrae and implant by tightening the nut 30 to the point that the barbs 88 are driven into the ventral surfaces of the bodies of the adjacent vertebrae to prevent rotation of the stabilizer bar 29 relative to the vertebrae.

Figure 11:
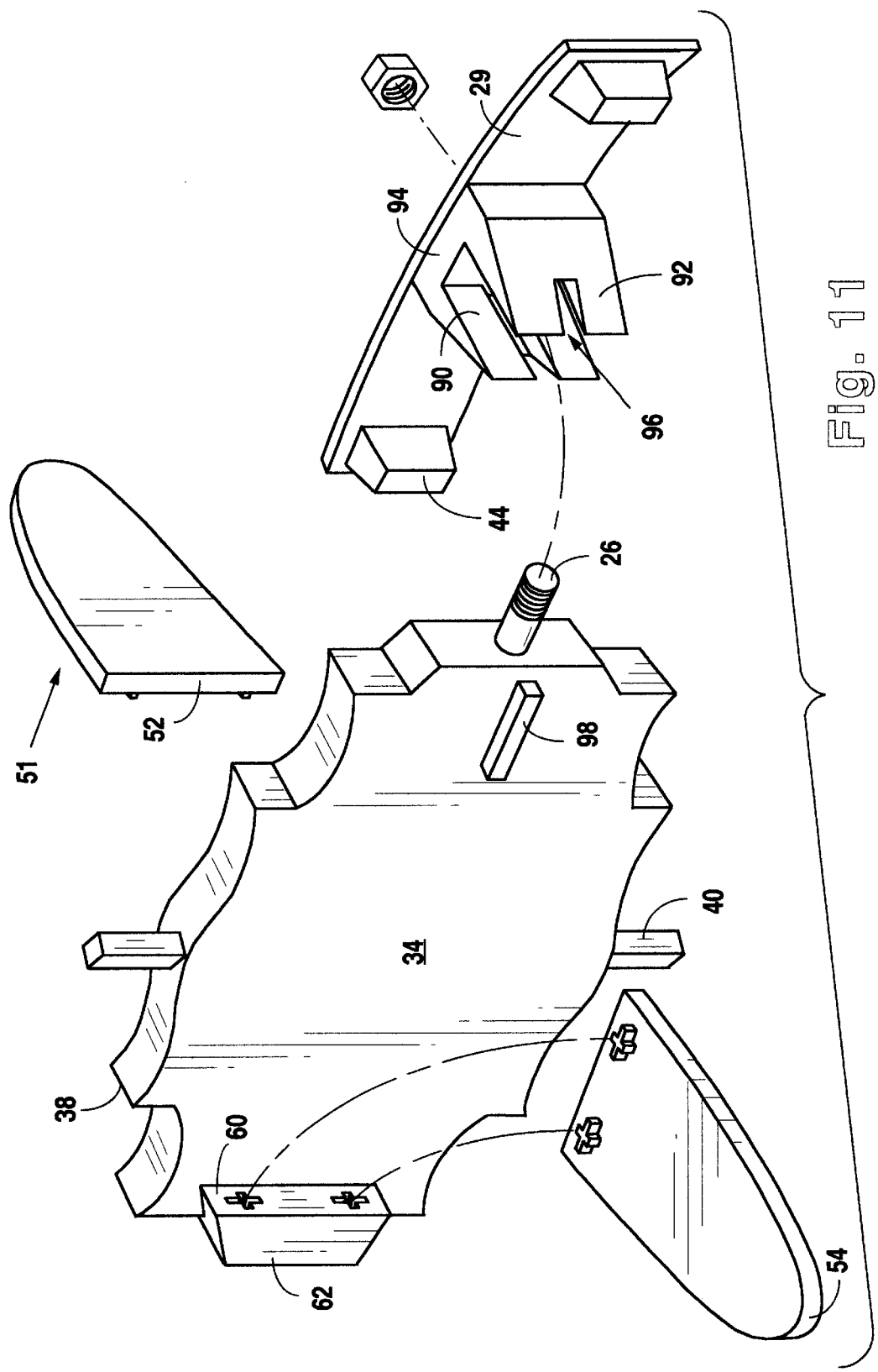
FIG. 11 is a perspective view of a sixth embodiment of a cervical stabilizer constructed in accordance with the teachings of the present invention.

In the embodiment shown in FIG. 11, rotation of the stabilizer bar 29 relative to implant 22 is prevented by the interaction of the inside surfaces 90 of the arms 92 of the U-shaped lock 94 which is formed integrally with the stabilizer bar 29 and the third and fourth surfaces 34 of implant 22. The surfaces 90 of lock 94 are provided with a slot 96 for receiving a complementary shaped key 98 on implant 22 to facilitate assembly of lock 94 to implant 22; those skilled in the art who have the benefit of this disclosure will recognize that the slot 96 may be located on the implant 22 and the key may be located on the lock 94 without any difference in the manner in which those component parts function. The lock 94 is provided with a bore (not shown) for receiving post 26 when the slot 96 is aligned with the key 98 on implant 22. In this embodiment, vertebrae bearing surfaces are provided on the ears 44 and on the top and bottom of lock 94.

Figure 12:
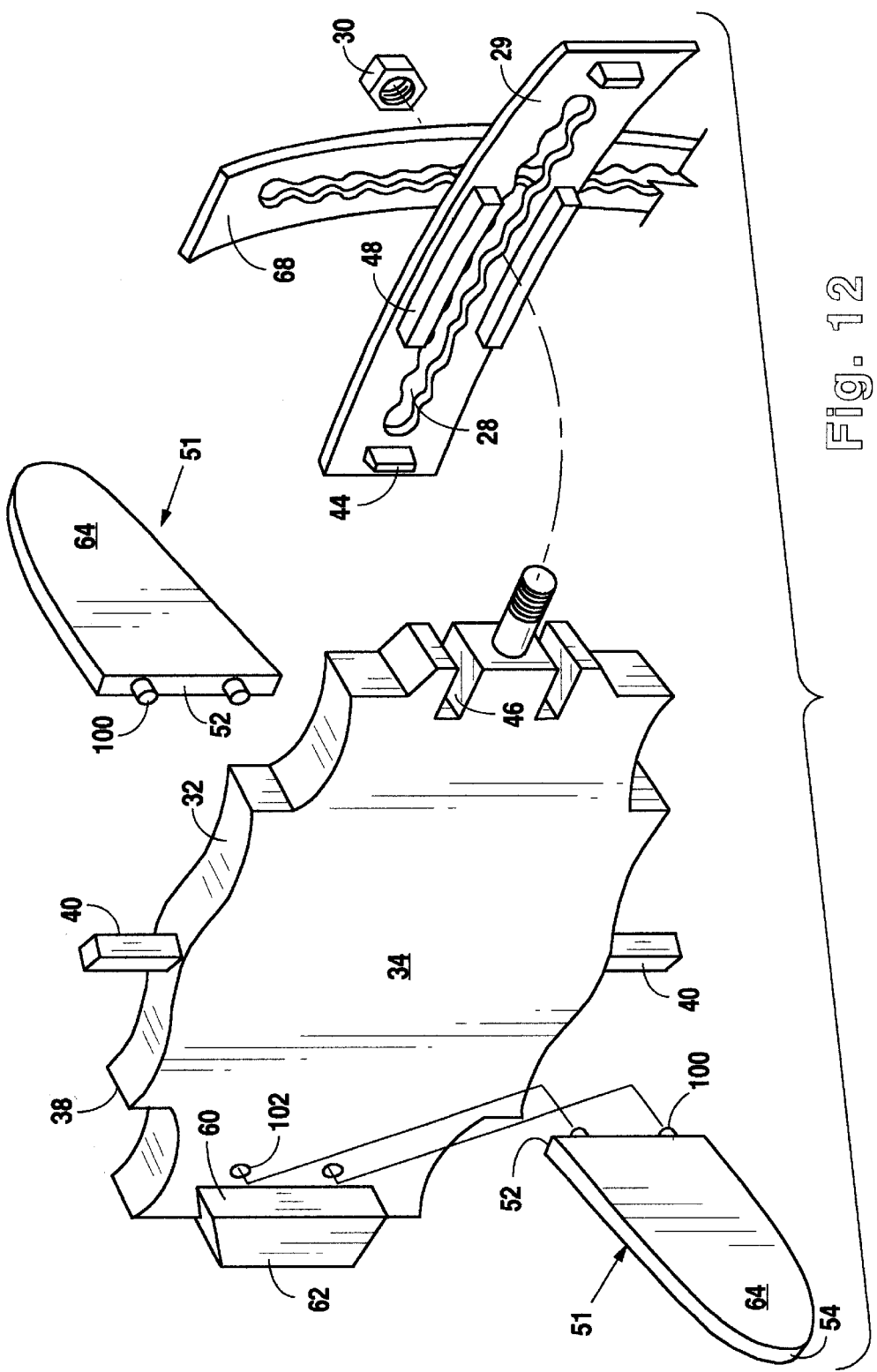
FIG. 12 is a perspective view of a seventh embodiment of a cervical stabilizer constructed in accordance with the teachings of the present invention.

Referring next to FIG. 12, it can be seen that in another alternative embodiment, the protectors 51 are provided with posts 100 similar to the posts 56 of the embodiment shown in FIGS. 1–6 for press-fitting into complementary-shaped slots 102 formed in the third and fourth surfaces 34 of implant 22. When the posts 100 are snapped into slots 102, the orthogonal surface 60 of end stop 62 abuts the sides, or flat surfaces, of protectors 51, thereby resisting pivotal movement of the protectors 51 relative to implant 22.

Referring once again to the embodiment shown in FIGS. 1–7, a preferred embodiment of the method of the present invention will now be described. Using spreaders such as those disclosed in International Application No. PCT/US95/00347, which reference is hereby incorporated into this specification in its entirety by this specific reference thereto, the vertebrae 16 and 18 are distracted to open the disk space, and once the desired "spread" is achieved, an implant 22 having a height H and width W selected to fit the disk space is then mounted on an applicator (not shown) by simply screwing the implant 22 into a complementary set of threads on the end of the applicator on the threads on post 26. The appropriately-sized implant 22 is then inserted into the disk space using the applicator 52 with the implant 22 oriented so that the top and bottom thereof, i.e., the first and second sides 32, engage the bodies of the adjacent vertebrae 16 and 18, respectively. Using the applicator, the implant 22 is then moved further into (or back out of) the disk space in an anterior-posterior direction so as to enable the implant 22 to be positioned in the disk space at a position in which the expanded, middle portion and the smaller width ends 25 and 36 of the third and fourth sides 34 of implant 22 contact the respective lower and upper surfaces of the bodies of the adjacent vertebrae 16 and 18 when rotated by approximately 90° using the applicator. The respective lower and upper surfaces of the vertebral bodies are slightly concave such that the larger width middle portion W" of implant 22 allows the implant 22 to engage substantially more of the respective surfaces of the vertebral bodies than conventional prosthetic devices, thereby providing increased stability to the fusion once further rotation of implant 22 in the disk space is prevented as described below.

Once positioned in the disk space so as to provide maximum stabilization and rotated by about 90° so that the first and second surfaces 32 of implant 22 contact the surfaces of the bodies of the adjacent vertebrae 16 and 18, the applicator is then detached from the implant 22 by unscrewing and backed out of the incision in the patient. The protectors 51 are then inserted into the disk space and press fit into place in the slots 58 formed in the orthogonal surface 60 of end stop 62. Referring to the alternative embodiments shown above, it can be seen that in those embodiments in which the means for positioning the protectors 51 comprises hinges or other such structure, the protectors 51 are pivoted from the first position in which the long axis of the protector is substantially parallel to the long axis of implant 22 to the second position in which the long axis of the protector is orthogonal to the long axis of the implant. The space within the disk space on either side of the implant 22 is then packed with cancellous bone chips.

After packing the disk space with bone chips, the stabilizer bar 29 is inserted through the same incision and positioned so that the ears 44 protrude into the disk space from the anterior aspect of the disk space (the patient's ventral side). Nut 30 is then threaded onto post 26 and tightened to mount the stabilizer bar 29 to implant 22 and hold the ears 44 in the disk space. Securing the stabilizer bar 29 to implant 22 in this manner prevents relative rotation between stabilizer bar 29 and implant 22 while the ears 44 of stabilizer bar 29 protrude into the disk space between the bodies of the adjacent vertebrae 16 and 18 so that the bearing surfaces 50 prevent rotation of the stabilizer bar 29 relative to the vertebrae 16 and 18. Those skilled in the art who have the benefit of this disclosure will recognize that the vertebrae bearing surfaces 50 bear against the cortical end plates of the respective vertebral bodies, which are comprised of non-cancellous bone, and which provide a hard, relatively smooth surface against which the surfaces 50 bear.

If necessary, a small amount of a physiologically compatible adhesive of a type known in the art is applied over the cancellous bone chips packed into the disk space on either side of the implant 22 to close off the remaining portion of the opening into the disk space. The patient should be able to sit up and ambulate soon after the procedure is completed because of the stability imparted to the cervical spine by the implant and method of the present invention. Before narrowing of the disk space occurs, the cancellous bone chips will have started the fusion process.

Although described in terms of the preferred embodiments shown in the figures, these embodiments are shown to exemplify the invention, it being recognized by those skilled in the art that certain changes can be made to the specific structure of the preferred embodiments shown and described without departing from the spirit of the present invention. Such changes may include, for instance, forming the implant 22 so that the first and second sides are substantially flat but not parallel along their longitudinal axes. The resulting wedge shape of the implant facilitates insertion of the implant into the disk space, the rounded end reducing the likelihood of injury to the nerves of the spinal cord during insertion into the disk space. Likewise, several combinations of positioning means, rotation preventing means, and shapes of the ears were described herein and those skilled in the art will recognize from this description that these combinations can be utilized in any of several different combinations with equal efficacy. All such modifications, and other modifications which do not depart from the spirit of the present invention, are intended to fall within the scope of the following claims.

What is claimed is:

1. A cervical disk stabilizer comprising:
    an elongate implant having a substantially rectangular cross-sectional shape for inserting between adjacent cervical vertebrae;
    a stabilizer bar for detachably mounting to one end of said implant to prevent relative motion between said implant and said stabilizer bar; and
    a surface formed on said stabilizer bar for contacting the adjacent cervical vertebrae to resist movement of said stabilizer bar relative to the adjacent cervical vertebrae.

2. The stabilizer of claim 1 additionally comprising a protector for mounting to the end of said implant opposite said stabilizer bar.

3. The stabilizer of claim 2 wherein said protector extends outwardly from said implant at an angle of about 90° relative to the longitudinal axis of said implant.

4. The stabilizer of claim 3 wherein the longitudinal axis of said stabilizer bar is positioned at an angle of about 90° to the longitudinal axis of said implant.

5. The stabilizer of claim 2 wherein said protector is pivotally mounted to said implant.

6. The stabilizer of claim 5 wherein said protector is pivoted from a first, folded position for inserting said implant into the space between adjacent cervical vertebrae and a second position extending outwardly from said implant at an angle relative to the longitudinal axis of said implant for closing off the dorsal aspect of the space between adjacent cervical vertebrae.

7. The stabilizer of claim 1 wherein said stabilizer bar is mounted to said implant so that the respective axes of said stabilizer bar and said implant are orthogonal.

8. The stabilizer of claim 1 wherein said stabilizer bar is curved to approximate the shape of the ventral aspect of the adjacent vertebrae.

9. The stabilizer of claim 1 additionally comprising a connector for detachably mounting to said implant when implanted between adjacent cervical vertebrae.

10. The stabilizer of claim 9 wherein said connector is mounted to a second implant.

11. The stabilizer of claim 1 additionally comprising means formed on said implant for preventing movement of said implant into or out of the space between two adjacent cervical vertebrae when inserted therebetween.

12. Apparatus for stabilizing two adjacent cervical vertebrae comprising:
    an elongate implant having a width dimension greater than the height dimension;
    a stabilizer bar having an ear formed thereon shaped to fit into the space between two adjacent cervical vertebrae;
    means formed on the first end of said implant for detachably mounting said stabilizer bar thereto with the axis of said stabilizer bar approximately perpendicular to the longitudinal axis of said implant; and
    a spinal cord protector for positioning on the second end of said implant for closing off the space between two adjacent cervical vertebrae when said implant is inserted therebetween.

13. The apparatus of claim 12 wherein the sides of said implant forming the height dimension thereof are provided with means for biting into bone when said implant is inserted into the space between two adjacent cervical vertebrae.

14. The apparatus of claim 12 wherein said mounting means comprises means for preventing rotation of said implant relative to said implant.

15. The apparatus of claim 12 wherein said spinal cord protector comprises first and second elongate members positioned on said implant at an angle from the longitudinal axis thereof.

16. The apparatus of claim 12 wherein said spinal cord protector comprises first and second elongate members positioned on said implant and movable from a first position folded against said implant to a second position extending substantially perpendicularly from the longitudinal axis of said implant.

17. The apparatus of claim 12 additionally comprising a connector mounted to said implant on the same end as said stabilizer bar for extending along the spinal column to stabilize the spine.

18. A stabilizer for insertion into the space from which the intervertebral disk has been removed from between two cervical vertebrae comprising:

an elongate implant having a substantially rectangular cross-sectional shape perpendicular to the length thereof comprised of first, second, third, and fourth sides providing a minimal height defined by the first and second sides and maximal width defined by the third and fourth sides, the third and fourth sides being arched from one end of said implant to the other to provide the middle portion of said implant with a bi-convex shape having a width larger than the width of the ends of said implant, the height being less than the width;

an elongate stabilizer bar for detachably mounting to said implant with the longitudinal axis thereof positioned at approximately a 90° angle to the longitudinal axis of said implant after said implant is inserted between two cervical vertebrae with the width dimension of said implant approximately perpendicular to the spinal column of the patient and rotated approximately 90° so that the width dimension is substantially parallel to the spinal column of the patient; and a vertebrae bearing surface formed on said stabilizer bar for engaging two adjacent cervical vertebrae after rotation of said implant in the disk space to prevent rotation of said stabilizer bar relative to the adjacent cervical vertebrae.

19. The stabilizer of claim 18 wherein said stabilizer bar is attached to the first end of said implant.

20. The stabilizer of claim 19 additionally comprising a protector detachably mounted to the second end of said implant.

* * * * *